United States Patent
Shoham (10) Patent No.: US 10,227,282 B2
(45) Date of Patent: *Mar. 12, 2019

(54) ANTI-VIRULENCE COMPOSITIONS AND METHODS

(71) Applicant: Case Western Reserve University, Cleveland, OH (US)

(72) Inventor: Menachem Shoham, Cleveland, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 213 days.

This patent is subject to a terminal disclaimer.

(21) Appl. No.: 14/445,713

(22) Filed: Jul. 29, 2014

(65) Prior Publication Data

US 2014/0336258 A1    Nov. 13, 2014

Related U.S. Application Data (63) Continuation of application No. 13/043,049, filed on Mar. 8, 2011, now Pat. No. 8,859,626.

(60) Provisional application No. 61/311,575, filed on Mar. 8, 2010.

(51) Int. Cl.

| | |
|---|---|
| *A61K 31/12* | (2006.01) |
| *A61K 45/06* | (2006.01) |
| *C07C 49/84* | (2006.01) |
| *C07C 65/24* | (2006.01) |
| *A61K 31/185* | (2006.01) |
| *A61K 31/192* | (2006.01) |
| *A61K 31/404* | (2006.01) |
| *C07C 309/44* | (2006.01) |
| *C07C 49/83* | (2006.01) |
| *A61K 31/166* | (2006.01) |
| *A61K 31/36* | (2006.01) |
| *C12N 1/36* | (2006.01) |

(52) U.S. Cl.
CPC .............. *C07C 49/83* (2013.01); *A61K 31/12* (2013.01); *A61K 31/166* (2013.01); *A61K 31/185* (2013.01); *A61K 31/192* (2013.01); *A61K 31/36* (2013.01); *A61K 31/404* (2013.01); *A61K 45/06* (2013.01); *C07C 49/84* (2013.01); *C07C 65/24* (2013.01); *C07C 309/44* (2013.01); *C12N 1/36* (2013.01); *C07C 2601/16* (2017.05)

(58) Field of Classification Search
CPC .... A61K 31/12; A61K 31/166; A61K 31/185; A61K 31/192; A61K 31/36; A61K 31/404; A61K 45/06; C07C 2601/16; C07C 309/44; C07C 49/83; C07C 49/84; C07C 65/24; C12N 1/36

See application file for complete search history.

(56) References Cited

U.S. PATENT DOCUMENTS

| | | | |
|---|---|---|---|
| 4,491,588 A * | 1/1985 | Rosenburg | A61K 31/415 514/254.07 |
| 5,025,036 A * | 6/1991 | Carson | C07C 45/46 514/533 |
| 5,191,108 A * | 3/1993 | Carson | C07C 45/46 560/54 |
| 6,136,771 A | 10/2000 | Taylor et al. | |
| 2004/0014818 A1 | 1/2004 | Boeck et al. | |
| 2007/0148185 A1* | 6/2007 | Rathore | C07K 14/445 424/191.1 |
| 2011/0016589 A1 | 1/2011 | Vaghchhipawala et al. | |
| 2011/0251162 A1 | 10/2011 | Liu et al. | |
| 2012/0040888 A1 | 2/2012 | Yeaman et al. | |

FOREIGN PATENT DOCUMENTS

WO    2010048630 A1    4/2010

OTHER PUBLICATIONS

Garazd et al. (Chemistry of Natural Compounds, 34, 4, 1998).*
Kao et al. (PNAS, 2002, 99, 15, 10066-10071).*
Handbook of Pharmaceutical Excipients (2006).*
Wiseman, Gordon, M., "The Hemolysis of Staphylococcus Aureus", Bacteriological Reviews, Dec. 1975, p. 317-344, The American Society for Microbiology.

* cited by examiner

*Primary Examiner* — Umamaheswari Ramachandran
(74) *Attorney, Agent, or Firm* — Tarolli, Sundheim, Covell & Tummino LLP (57) ABSTRACT

A method of reducing the virulence of a bacterium that expresses accessory gene regulator A (AgrA) includes administering to the bacterium an amount of AgrA antagonist effective to inhibit the synthesis of one or more virulence factors by the bacterium.

2 Claims, 9 Drawing Sheets

ANTI-VIRULENCE COMPOSITIONS AND METHODS

RELATED APPLICATION

This application claims priority from U.S. Provisional Application No. 61/311,575, filed Mar. 8, 2010, the subject matter of which, are incorporated herein by reference in their entirety.

TECHNICAL FIELD

This application relates to anti-virulence compositions and methods for treating bacterial infections and more particularly to compositions and methods for reducing the virulence of bacterium that expresses accessory gene regulator A (AgrA).

BACKGROUND

*Staphylococcus* is one of the most common causes of hospital-acquired and community-acquired infections worldwide, and reports of its growing levels of resistance to last-resort antibiotics, such as vancomycin, threaten a serious international public health problem. *Staphylococcus aureus* causes diseases ranging from minor skin infections to life-threatening deep infections such as pneumonia, endocarditis, meningitis, post-operative wound infections, septicemia, and toxic shock syndrome. *Staphylococcus* causes such fatal diseases due to the expression of toxins and other virulence factors that have been shown to affect the outcome of the infective process. The expression of virulence factors is highly regulated and involves cell-cell communication, otherwise known as quorum sensing. Therefore, alternative methods for the prevention and treatment of bacterial infections in general and antibiotic resistant *S. aureus* infections in particular are needed.

SUMMARY

This application relates to anti-virulence compositions and methods for treating bacterial infections and more particularly to compositions and methods for reducing the virulence of bacterium that expresses accessory gene regulator A (AgrA).

An aspect of the application relates to a method of reducing the virulence of a bacterium that expresses accessory gene regulator A (AgrA). The method includes administering to the bacterium an amount of AgrA antagonist effective to inhibit the synthesis of one or more virulence factors by the bacterium. The AgrA antagonist can include at least one of a substituted phenyl(benzoic acid), a phenyl or substituted phenyl linked to a substituted aryl by a linker that is one to three atoms, a substituted naphthalene, or pharmaceutically acceptable salts thereof.

Another aspect of the application relates to a method of treating a bacterial infection in a subject. The method includes administering to the subject an amount of AgrA antagonist effective to inhibit the synthesis of one or more virulence factors by the bacteria. The AgrA antagonist can include at least one of a substituted phenyl(benzoic acid), a phenyl or substituted phenyl linked to a substituted aryl by a linker that is one to three atoms, a substituted naphthalene, or pharmaceutically acceptable salts thereof.

A further aspect of the application relates to a method of treating a bacterial infection related disease or disorder in a subject. The method includes administering to the subject an amount of AgrA antagonist effective to inhibit the synthesis of one or more virulence factors by the bacteria. The AgrA antagonist can include at least one of a substituted phenyl (benzoic acid), a phenyl or substituted phenyl linked to a substituted aryl by a linker that is one to three atoms, a substituted naphthalene, or pharmaceutically acceptable salts thereof.

Another aspect of the application relates to a method of screening a compound effective in reducing the virulence of a *Staphylococcus* bacterium. The method includes generating a model of an AgrA N-terminal phosphoryl-binding pocket centered on Asp 59, and quantifying a level of interaction energy of the compound as docked to the AgrA N-terminal phosphoryl-binding pocket centered on Asp 59, wherein a compound having a lower interaction energy compared to a control is indicative of an effective compound.

DETAILED DESCRIPTION

Methods involving conventional molecular biology techniques are described herein. Such techniques are generally known in the art and are described in detail in methodology treatises, such as *Current Protocols in Molecular Biology*, ed. Ausubel et al., Greene Publishing and Wiley-Interscience, New York, 1992 (with periodic updates). Unless otherwise defined, all technical terms used herein have the same meaning as commonly understood by one of ordinary skill in the art to which the present invention pertains.

Commonly understood definitions of molecular biology terms can be found in, for example, Lodish et al., *Molecular Cell Biology*, 6th Edition, W. H. Freeman: New York, 2007, and Lewin, *Genes IX*, Jones and Bartlett Publishers: Mass., 2008. The definitions provided herein are to facilitate understanding of certain terms used frequently herein and are not meant to limit the scope of the application.

The terms "reducing", "suppressing" and "inhibiting" have their commonly understood meaning of lessening or decreasing.

The terms "effective," "effective amount," and "therapeutically effective amount" refer to that amount of an AgrA antagonist and/or a pharmaceutical composition thereof that inhibits the synthesis of one or more virulence factors by a bacterium or that results in amelioration of symptoms or a prolongation of survival in a subject with a bacteria related disease or disorder.

The term "treatment" or "treating" refers to any therapeutic intervention in a mammal, including: (i) prevention, that is, causing the clinical symptoms not to develop, e.g., preventing infection from occurring and/or developing to a harmful state; (ii) inhibition, that is, arresting the development of clinical symptoms, e.g., stopping an ongoing infection so that the infection is eliminated completely or to the degree that it is no longer harmful; and/or (iii) relief, that is, causing the regression of clinical symptoms, e.g., causing a relief of fever and/or inflammation caused by an infection.

The terms "pharmaceutically acceptable" or "therapeutically acceptable" refers to a substance which does not interfere with the effectiveness or the biological activity of the active ingredients and which is not toxic to the host.

The terms "host" or "subject" refers to any mammal including, but not limited to, human beings, rats, mice, dogs, goats, sheep, horses, monkeys, apes, rabbits, cattle, etc. Typically, the terms "host," "patient," and "subject" are used interchangeably herein in reference to a human subject.

The term "in vitro" refers to an artificial environment and to processes or reactions that occur within an artificial environment. In vitro environments include, but are not limited to, test tubes and cell culture. The term "in vivo" refers to the natural environment (e.g., an animal or a cell) and to processes or reaction that occur within a natural environment. The term "in silico" refers to a process that is performed on a computer or is simulated on a computer or in virtual reality.

The term "AgrA antagonist" refers to any molecule with the capability of substantially reducing or inhibiting the activity of AgrA, by blocking with some degree of effectiveness, the phospho-histidine pocket of AgrA. This invention focuses most strongly on small molecules as AgrA antagonists which can be identified by the methods set forth herein.

The term "small molecule" can refer to lipids, carbohydrates, polynucleotides, polypeptides, or any other organic or inorganic molecules.

The phrase "having the formula" or "having the structure" is not intended to be limiting and is used in the same way that the term "comprising" is commonly used.

This application relates to anti-virulence compositions and methods for treating bacterial infections and more particularly to compositions and methods for reducing the virulence of bacterium that expresses accessory gene regulator A (AgrA).

Figure 1:
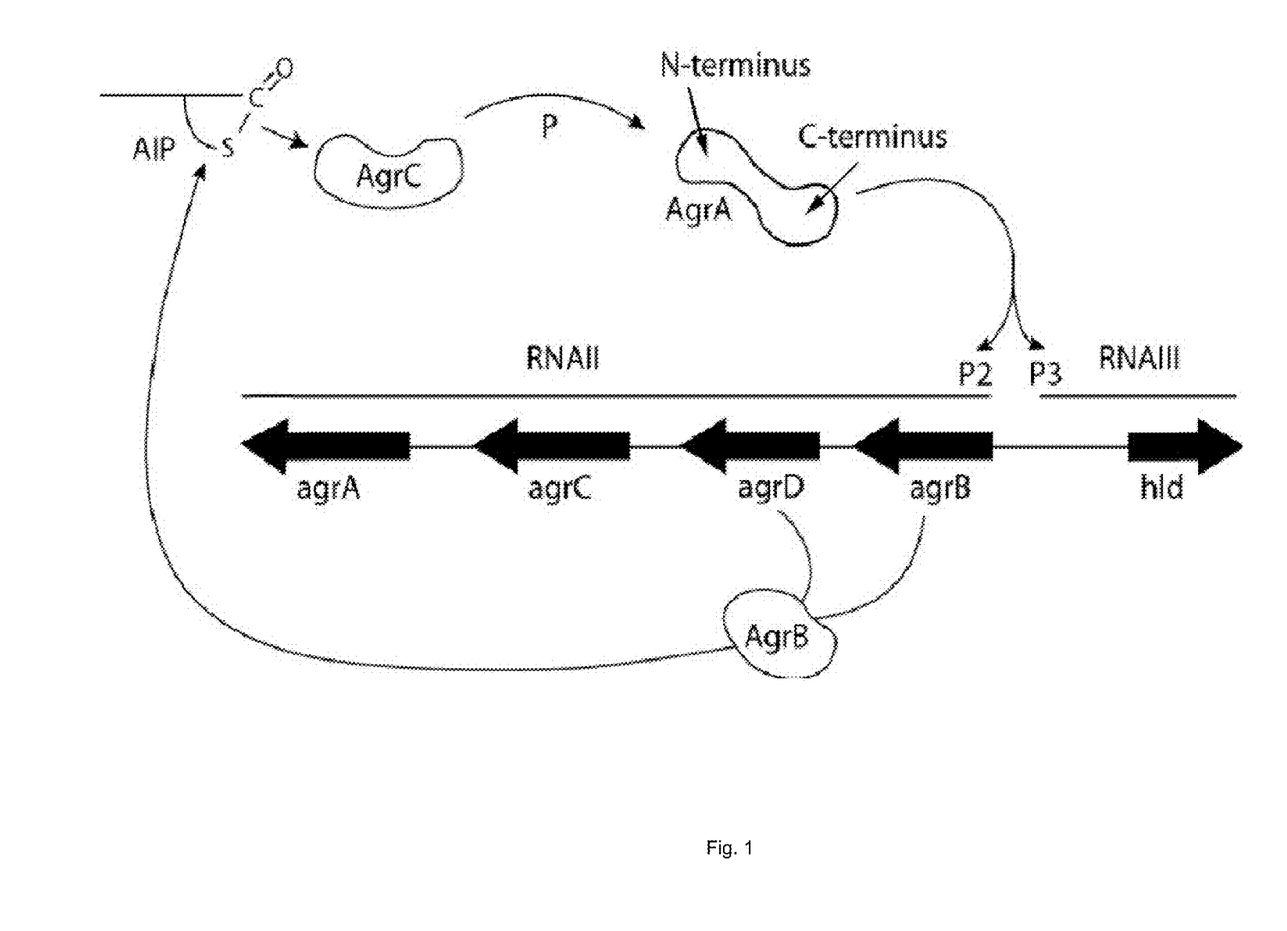
FIG. 1 illustrates a schematic representation of the agr operon that regulates virulence in Staphylococci.

The accessory gene regulator (agr) system represents an operon that controls the expression of virulence factors in Gram-positive bacteria (Kleerebezem M, Quadri L E, Kuipers O P and de Vos W M (1997) Quorum sensing by peptide pheromones and two-component signal-transduction systems in Gram-positive bacteria. *Molecular Microbiology* 24:895). The agr operon contains two sets of genes that code for two sets of mRNA called RNAII and RNAIII. The two parts of the operon are transcribed in opposite directions, each with its own promoter P2 and P3 (FIG. 1).

The products of the agr system include the autoinducer peptide (AIP), encoded by AgrD and processed and exported by AgrB. The thiolactone AIP binds to and activates the histidine kinase AgrC, which in turn binds to the N-terminal domain of AgrA to phosphorylate an aspartate residue in the binding pocket. The C-terminal DNA-binding domain of AgrA acts as a transcription factor that activates both promoters P2 and P3. Consequently, phosphorylated AgrA promotes further production of AIP in the autocatalytic RNAII cycle via the P2 promoter and concomitantly activates P3 leading to the induction of RNAIII. Being the effector of the agr system, RNAIII initiates the transcription of genes that encode a variety of virulence factors, e.g., hla (encoding $\alpha$-hemolysin), psm-$\alpha$ (phenol-soluble modulin-$\alpha$), saeB (enterotoxin B), tst (TSST-1), ssp and spr (serine proteases). Compounds and methods that can block phosphorylation and activation of AgrA in bacterium expressing AgrA can therefore inhibit the production and excretion of one or more bacterium virulence factors and be used to treat or prevent bacterium infections.

An aspect of the application therefore relates to a method of reducing the virulence of a bacterium that expresses AgrA by administering to the bacterium an amount of AgrA antagonist effective to inhibit the synthesis of one or more virulence factors by the bacterium.

Bacteria in accordance with this application that can be treated with the AgrA antagonist can include those associated with pathogenic association with another organism, bacterial infection, and widespread disease. In some embodiments, bacteria treated by the AgrA antagonist can include gram-positive bacteria, such as *Staphylococcus* and *Streptococcus*. In some embodiments, the bacteria can be antibiotic resistant methicillin-resistant *Staphylococcus aureus* (MRSA). In other embodiments, the bacteria can be *Streptococcus pyogenes*.

Virulence factors as contemplated herein include any molecules expressed and secreted by bacteria to promote colonization and/or adhesion in a host subject, promote evasion of the host's immune response and obtain nutrition from the host subject. Virulence factors can also include both exotoxins and endotoxins.

Non-limiting examples of virulence factors inhibited by an AgrA antagonist described herein include one or more of a protease (e.g., serine proteases), nuclease, lipase, coagulase, hyaluronidase, clumping factor, pyrogenic toxin superantigen (e.g., TSST-1), enterotoxins (e.g., enterotoxin B), exfoliative toxin, leukotoxin, along with $\alpha$, $\beta$, $\gamma$, $\gamma$-variant, and $\delta$-hemolysins. In some aspects, the virulence factor inhibited is $\alpha$-hemolysin.

In an aspect of the application, the AgrA antagonist can include a small molecule effective in inhibiting the phosphorylation of the AgrA N-terminal phosphoryl-binding pocket centered on residue Asp 59. It was found using a 3-D homology model (FIG. 2) that an AgrA phosphoryl-binding pocket is centered on residue Asp 59 of the N-terminal regulatory domain of ArgA. Small molecule compounds that can block the N-terminal phosphoryl-binding pocket of AgrA can also potentially inhibit AgrA transcription factor activity. Inhibition of AgrA transcription factor activity can in turn inhibit the synthesis of one or more virulence factors by the bacterium and be used to treat or prevent bacterial infection and particularly MRSA.

In certain embodiments, small molecule compounds that affect (e.g., reduces, inhibits, eliminates, or ameliorates) the activity of AgrA and that can be used as an AgrA antagonist as described can include at least one of a substituted phenyl (benzoic acid), a phenyl or substituted phenyl linked to a substituted aryl by a linker that is one to three atoms, a substituted naphthalene, or pharmaceutical salts thereof.

In some embodiments, the phenyl or substituted phenyl linked to a substituted aryl by a linker that is one to three atoms can have the general formula:

wherein $R_1$, $R_2$, $R_3$, $R_4$, and $R_5$ are each independently selected from the group consisting of H, hydroxy, carboxy, lower (C1-C6) alkoxy, lower (C1-C6) alkoxyhydroxy, lower (C1-C6) alkyl, alkenyl, sulfonic, and halo (e.g., Cl, F, or Br); and Y is selected from the group consisting of O, carboxy, and lower (C1-C6) alkanoyloxy; and pharmaceutically acceptable salts thereof.

In other embodiments, the phenyl or substituted phenyl linked to a substituted aryl by a linker that is one to three atoms has a formula selected from the group consisting of:

(VI)

(IX)

(XI)

(XII)

(XIV)

and pharmaceutically acceptable salts thereof.

In some embodiments, the substituted phenyl(benzoic acid) has the general formula:

wherein $R_6$, $R_7$, and $R_8$ are each independently selected from the group consisting of hydrogen, a halo (e.g., Cl, F, or Br), and hydroxyl; and pharmaceutically acceptable salts thereof.

In other embodiments, the substituted phenyl(benzoic acid) has a formula selected from group consisting of:

(I)

(VII)

(II)

(X)

(III)

(XIII)

(IV)

(XV)

(V)

(XVI)

(VI)

(VII)

and pharmaceutically acceptable salts thereof.

In still other embodiments of the application, the AgrA antagonist can include at least one of the following formulas:

and pharmaceutically acceptable salts thereof. As shown in the Example, These compounds (i.e., compounds I-XVI) were found to substantially inhibit α-hemolysin production of *Staphylococcus* (MRSA strain USA3000) and/or *Streptococcus* without affecting the growth of the bacteria. Moreover, compounds I-VII were found to inhibit AgrA, AgrC, α-hemolysin, phenol-soluble modulin-α (psmα), and RNAIII gene expression in MRSA strain USA300.

Additional AgrA antagonists for use in the application can be identified by screening compounds for the ability to inhibit AgrA activity. Of particular interest is the screening of compounds that have a low toxicity for human cells and/or high specificity for gram positive bacteria, such as *Staphylococcus* and *Streptococcus*, preferably with substantially little or no pressure for selection of strains resistant to the action of the compound, and without substantially affecting normal flora of the host subject (e.g., as distinguished from wide-spectrum antibiotics). Toxicity may be quantified in a simple assay wherein bacteria are left to grow planktonic in the absence or presence of various concentrations of a test compound. In such assays, it is contemplated that the concentration of a test compound would be about 1 mg/L, about 5 mg/L, about 10 mg/L, about 20 mg/L, about 50 mg/L and/or about 100 mg/L.

Candidate antagonists of ArgA can be screened for function by a variety of techniques known in the art and/or disclosed within the instant application, such as an ELISA.

Candidate compounds may be screened individually, in combination, or as a library of compounds.

Candidate compounds screened include chemical compounds. In some aspects of the application, the candidate compound is a small organic molecule having a molecular weight of more than about 50 and less than about 2,500 daltons. Compounds screened are also found among biomolecules including, but not limited to: peptides, saccharides, fatty acids, steroids, pheromones, purines, pyrimidines, derivatives, structural analogs or combinations thereof. The compounds screened can include functional groups necessary for structural interaction with proteins, particularly hydrogen bonding, and typically include at least an amine, carbonyl, hydroxyl, or carboxyl group. In some embodiments, the screened compounds can include biaryl and naphthalene derivatives that have a similar structure to previous identified compounds.

Candidate compounds are obtained from a wide variety of sources including libraries of synthetic or natural compounds. Compounds to be screened can be produced, for example, by bacteria, yeast or other organisms (e.g., natural products), produced chemically (e.g., small molecules, including peptidomimetics), or produced recombinantly. It is further contemplated that natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

In many drug screening programs, with test libraries of compounds and natural extracts, high throughput assays are desirable in order to maximize the number of compounds surveyed in a given period of time. Assays of the present invention may be developed with purified or semi-purified proteins or with lysates. These assays are often preferred as "primary" screens in that they can be generated to permit rapid development and relatively easy detection of an alteration in a molecular target, which is mediated by a test agent. Assays of the present invention can include cell-based assays. Cell-based assays may be performed as either a primary screen, or as a secondary screen to confirm the activity of compounds identified in a cell free screen, such as an in silico screen.

This application also relates to a method of screening in silico for a compound effective in blocking phosphorylation of an AgrA N-terminal phosphoryl-binding pocket centered on residue Asp 59. As shown in the Example below and in FIG. 2, a 3-D model of the N-terminal regulatory domain of AgrA can be built using the 3-D structure of a homologous protein. The sequence of AgrA N terminal domain (AgrA N) can be compared against the protein sequences in the Protein Data Bank using a BLAST search to identify a homologous protein. In some aspects, the degree of sequence identity of the homologous protein must be greater than about 20%. An initial model can then be generated using a suitable protein modeling software program. In some aspects, the model can then be subjected to energy refinement with software program CNS.

Once a model is built, small molecule AgrA antagonists that block the N-terminal phosphoryl-binding pocket of AgrA centered on Asp 59 can be determined by methods well known in the relevant art using in silico conformation screening techniques. In one example, virtual screening of the National Cancer Institute-Frederick Scientific (NCI) Library of small molecules, downloaded from the publicly available ZINC database, can be performed using a multi-processor Linux-based workstation with drug discovery software (e.g., program GLIDE within the drug discovery software suite from Schrödinger LLC. (Portland, Oreg.)).

In some aspects of the invention, candidate compounds, including those collected from an in silico similarity search, may be further screened for efficacy using in vitro and/or in vivo experimental screening methods described herein. The efficacy of an identified compound can be assessed by generating dose response curves from data obtained using various concentrations of the test compound. Moreover, a control assay can also be performed to provide a baseline for comparison. Such candidates can be further tested for their ability to: inhibit phosphorylation of the AgrA Asp 59 residue in vitro; inhibit AgrA C-terminal DNA binding activity in vitro; inhibit AgrA transcription factor activity in vitro; inhibit the synthesis of one or more virulence factors by a bacterium (e.g., *Staphylococcus* and/or *Streptococcus* bacterium) in vitro; reduce the virulence of a bacterium (e.g., *Staphylococcus* and/or *Streptococcus* bacterium) in vitro or in vivo; and/or for other properties, such as the ability to protect in vivo against bacterial infection.

In some aspects, the efficacy of the compound can be tested in vivo in animal models. Compounds having a desired activity as determined in the assays described above can be further screened for their ability to affect bacterium (e.g., *Staphylococcus* and/or *Streptococcus* bacterium) virulence factor production, and to affect bacterial infection, in a non-human animal model. The animal model selected will vary with a number of factors including, but not limited to, the particular pathogenic strain of bacteria (e.g., MRSA USA300) against which candidate compounds are to be screened, the ultimate subject for which the candidate compounds are to serve as therapeutics, etc. Animals that can be used in screening assays include any animal susceptible to infection by the selected bacteria species. For example, where the *Staphylococcus* species is *S. aureus*, the animal model can be a rodent model, preferably a mouse model.

In general, the candidate compound is administered to a non-human animal susceptible to bacterial infection, where the animal has been previously infected with the bacterium or receives an infectious dose of the bacterium in conjunction with the candidate compound. The candidate compound can be administered in any manner desired and/or appropriate for delivery of the compound in order to affect a desired result. For example, the candidate compound can be administered by injection (e.g., by injection intravenously, intramuscularly, subcutaneously, or directly into the tissue in which the desired affect is to be achieved), topically, orally, or by any other desirable means. Normally, this screen will involve a number of animals receiving varying amounts and concentrations of the candidate compounds (from no compound to an amount of compound that approaches an upper limit of the amount that can be delivered successfully to the animal), and may include delivery of the compound in different formulations. The compounds can be administered singly or can be combined in combinations of two or more, especially where administration of a combination of compounds may result in a synergistic effect.

The effect of compound administration upon the animal model can be monitored by any suitable method, such as assessing the number and size of bacteria-associated lesions, overall health, survival rate, etc. Where the candidate compound affects bacterial infection in a desirable manner (e.g., by reducing infectious load, facilitating lesion regression, extending lifetime, etc.), the candidate compound is identified as an effective compound for use in treatment of bacterial infection in a subject.

In another aspect of the application, AgrA antagonists are provided in the form of pharmaceutical compositions. A pharmaceutical composition including at least one AgrA antagonist will typically further include a conventional pharmaceutical carrier or excipients, including solid, semi-solid, liquid or aerosol dosage forms, such as, for example, tablets, capsules, powders, liquids, gels, suspensions, suppositories, aerosols or the like. In addition, these compositions may include additional active therapeutic agents, adjuvants, etc.

Pharmaceutical compositions including AgrA antagonists are administered at a therapeutically effective dosage, e.g., a dosage sufficient to improve the chance of successful prevention or treatment of infection or related disease or disorder. Generally, depending on the intended mode of administration, the pharmaceutically acceptable composition will contain about 0.1% to 100 wt. %, preferably about 0.5% to about 50%, by weight of active compound, the remainder being suitable pharmaceutical excipients, carriers, etc. Actual methods for preparing such dosage forms are known, or will be apparent, to those skilled in this art. For example, see Remington the Science and Practice of Pharmacy, 21$^{th}$ ed., Lippincott Williams & Wilkins (2005). Any of the foregoing pharmaceutical compositions may be appropriate in methods in accordance with the present invention, provided that the AgrA antagonist in the composition is not inactivated by the composition and the composition is physiologically compatible.

The pharmaceutical compositions can be administered to any animal that can experience the beneficial effects of an AgrA antagonist described herein. In some aspects the animal is a human. The pharmaceutical compositions described herein can be administered by any means that achieve their intended purpose. For example, administration can be by parenteral, topical, local, subcutaneous, oral, intravenous, intraarticular, intrathecal, intramuscular, intraperitoneal, or intradermal delivery, or by transdermal, buccal, oromucosal, ocular routes or via inhalation. In some aspects, administration to a subject is systemic. In other aspects, administration to a subject is local, such as in a topical solution, topical ointment, or topical cream.

An AgrA antagonist or pharmaceutical compound of the invention, can be administered prior to infection, after infection but prior to the manifestation of symptoms of a disease of disorder associated with the infection, or after the manifestation of symptoms associated with the production one or more bacterial virulence factors to prevent further bacterial multiplication and to prevent further production of virulence factors thereby hindering development of the disease or its progression.

It will be understood, however, that the total daily usage of the AgrA antagonist in a therapeutic method described herein will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

In another aspect of the application, a pharmaceutical composition including an AgrA antagonist can further include an antibacterial therapeutic. Exemplary antibacterial therapeutics include, but are not limited to, colloidal silver, penicillin, penicillin G, erythromycin, polymyxin B, viomycin, chloromycetin, streptomycins, cefazolin, ampicillin, methicillin, oxacillin, nafcillin, cloxacillin, dicloxacillin azactam, tobramycin, cephalosporins (including cephalothin, cefazolin, cephalexin, cephradine, cefamandole, cefoxitin, and 3rd-generation cephalosporins), carbapenems (including imipenem, meropenem, Biapenem), bacitracin, tetracycline, doxycycline, gentamycin, quinolines, neomycin, clindamycin, kanamycin, metronidazole, treptogramins (including Quinupristin/dalfopristun (Synercid™)), Streptomycin, Ceftriaxone, Cefotaxime, Rifampin, glycopeptides (including vancomycin, teicoplanin, LY-333328 (Ortivancin), dalbavancin), macrolides (including erythromycin, clarithromycin, azithromycin, lincomycin, and clindamycin), ketolides (including Telithromycin, ABT-773), tetracyclines, glycylcyclines (including Terbutyl-minocycline (GAR-936)), aminoglycosides, chloramphenicol, Imipenem-cilastatin, fluoroquinolones (including ofloxacin, sparfioxacin, gemifloxacin, cinafloxacun (DU-6859a)) and other topoisomerase inhibitors, Trimethoprim-sulfamethoxazole (TMP-SMX), Ciprofloxacin, topical mupirocin, Oxazolidinones (including AZD-2563, Linezolid (ZyvoX™)), Lipopeptides (including Daptomycin, Ramoplanin), ARBELIC (TD-6424) (Theravance), TD6424 (Theravance), isoniazid (INN), rifampin (RIF), pyrazinamide (PZA), Ethambutol (EMB), Capreomycin, cycloserine, ethionamide (ETH), kanamycun, and p-aminosalicylic acid (PAS).

The combination of an AgrA antagonist with one or more additional antibacterial therapeutics in a method of the present invention may reduce the amount of either pharmaceutical compound needed as a therapeutically effective dosage, and thereby reduce any negative side effects the agents may induce in vivo. In addition, the combination of an AgrA antagonist with one or more additional antibacterial therapeutics in a method described herein may reduce the MIC (minimum inhibitory concentration) of the antibacterial therapeutic, which in turn reduces the opportunity for microbial resistance to specific antibacterial therapeutics. Combination therapies may involve co-administration or sequential administration of the pharmaceutically active components.

In some aspects, treatment with an AgrA antagonist may precede or follow the treatment with an additional antibacterial therapeutic, including intervals ranging from minutes to weeks. In some aspects of the invention where the AgrA antagonist and the additional antibacterial therapeutic are administered separately (either in separate compositions administered simultaneously or in separate compositions administered at different time intervals), one would generally ensure that a significant period of time did not expire between the times of each delivery, such that the additional antibacterial therapeutic and the AgrA antagonist would still be able to exert an advantageously combined effect. In such instances, it is contemplated that one would administer both therapeutics within about 1, about 2, about 3, about 4, about 5, about 5, about 6, about 7, about 8, about 9, about 10, about 11, about 12, about 13, about 14, about 15, about 16, about 17, about 18, about 19, about 20, about 21, about 22, about 23, about 24, about 36, about 48, or about 72 hours of each other. In one aspect, both therapeutics are administered within about 6-12 hours of each other. In some situations, it may be desirable to extend the time period for treatment significantly.

It is further contemplated that AgrA antagonist and pharmaceutical compositions thereof described herein can be used in preventative and therapeutic treatments for infection of pathogenic bacterium, such as *Staphylococcus* or *Streptococcus*. The rationale behind treatment of a subject with an AgrA antagonist is multifaceted. By preventing the synthesis and excretion of virulence factors, the pathogenecity of the invading organism is diminished, or even eliminated. Furthermore, AgrA may itself have an adverse effect on the immune system of the host subject independent of RNAIII. For example, it is contemplated that AgrA antagonist mediated inhibition of phenol-soluble modulins (PSMs), which play a role in the immune evasion of *S. aureus*, can provide a beneficial effect.

Therefore, another aspect of the invention provides a method of treating a bacterial infection in a subject. The method includes administering to the subject a therapeutically effective amount of an AgrA antagonist, wherein the AgrA antagonist when administered to the subject reduces the virulence of the bacterial infection.

An AgrA antagonist described herein can be used to prevent or treat infection of a subject by any bacteria species that utilizes the AgrA response regulator in quorum sensing and the production of virulence factors. The AgrA antagonists of the invention are typically administered to subjects having or at risk of having a bacterial infection (e.g., *Staphylococcus* and/or *Streptococcus* infection). For example, a subject that can benefit from treatment with an AgrA antagonist described herein can be a hospital patient at risk of developing nosocomial infection or a subject known to be infected with or having been exposed to antibiotic resistant bacteria such as, for example, Methicillin-resistant *S. aureus*, Vancomycin-intermediary-sensible *S. aureus*, and Vancomycin-resistant *S. aureus*. Methods of detecting the presence of a *Staphylococcus* bacterial infection are well known, for example, by culturing from a sample from the subject, e.g. a blood culture, can be used.

In addition, an AgrA antagonist described herein or identified by a method of the invention can be administered to a subject to inhibit the activity of AgrA thereby preventing the production of virulence factors that aid in bacterial infection or development of a disease condition or disorder associated with the bacterial infection. Examples of diseases and disorders associated with a bacterial infection responsive to AgrA antagonist treatment can include, without limitation, postoperative wound infections, bacteraemia, septic arthritis, pneumonia, osteomyelitis, meningitis, mastitis, erysipelas, cellulitis, sepsis, acute endocarditis, furuncles, carbuncles, superficial abscesses, deep abscesses in various organs, impetigo, food poisoning, gastroenteritis, urinary tract infection, toxic shock syndrome, and scalded skin syndrome.

Additionally, percutaneous devices (such as catheters) and implanted medical devices (including, but not limited to, pacemakers, vascular grafts, stents, and heart valves) commonly serve as foci for bacterial infection. The tendency of some microorganisms (e.g., *Staphylococcus* bacteria) to adhere to and colonize the surface of the device, promotes such infections, which increase the morbidity and mortality associated with use of the devices. Therefore, in another aspect, an AgrA antagonist or pharmaceutical compositions thereof can be used to virulence of bacteria on or associated with a medical device by contacting the device with an AgrA antagonist or pharmaceutical composition thereof in an amount effective to inhibit the synthesis of one or more virulence factors by the bacterium.

A medical device according to the application can comprise any instrument, implement, machine, contrivance, implant, or other similar or related article, including a component or part, or accessory which is: recognized in the official U.S. National Formulary the U.S. Pharmacopoeia, or any supplement thereof; intended for use in the diagnosis of disease or other conditions, or in the cure, mitigation, treatment, or prevention of disease, in humans or in other animals; or, intended to affect the structure or any function of the body of humans or other animals, and which does not achieve any of its primary intended purposes through chemical action within or on the body of human or other animal, and which is not dependent upon being metabolized for the achievement of any of its primary intended purposes.

A medical device can include, for example, endovascular medical devices, such as intracoronary medical devices. Examples of intracoronary medical devices can include stents, drug delivery catheters, grafts, and drug delivery balloons utilized in the vasculature of a subject. Where the medical device comprises a stent, the stent may include peripheral stents, peripheral coronary stents, degradable coronary stents, non-degradable coronary stents, self-expanding stents, balloon-expanded stents, and esophageal stents. The medical device may also include arterio-venous grafts, by-pass grafts, penile implants, vascular implants and grafts, intravenous catheters, small diameter grafts, artificial lung catheters, electrophysiology catheters, bone pins, suture anchors, blood pressure and stent graft catheters, breast implants, benign prostatic hyperplasia and prostate cancer implants, bone repair/augmentation devices, breast implants, orthopedic joint implants, dental implants, implanted drug infusion tubes, oncological implants, pain management implants, neurological catheters, central venous access catheters, catheter cuff, vascular access catheters, urological catheters/implants, atherectomy catheters, clot extraction catheters, PTA catheters, PTCA catheters, stylets (vascular and non-vascular), drug infusion catheters, angiographic catheters, hemodialysis catheters, neurovascular balloon catheters, thoracic cavity suction drainage catheters, electrophysiology catheters, stroke therapy catheters, abscess drainage catheters, biliary drainage products, dialysis catheters, central venous access catheters, and parental feeding catheters.

The medical device may additionally include either arterial or venous pacemakers, vascular grafts, sphincter devices, urethral devices, bladder devices, renal devices, gastroenteral and anastomotic devices, vertebral disks, hemostatic barriers, clamps, surgical staples/sutures/screws/plates/wires/clips, glucose sensors, blood oxygenator tubing, blood oxygenator membranes, blood bags, birth control/IUDs and associated pregnancy control devices, cartilage repair devices, orthopedic fracture repairs, tissue scaffolds, CSF shunts, dental fracture repair devices, intravitreal drug delivery devices, nerve regeneration conduits, electrostimulation leads, spinal/orthopedic repair devices, wound dressings, embolic protection filters, abdominal aortic aneurysm grafts and devices, neuroaneurysm treatment coils, hemodialysis devices, uterine bleeding patches, anastomotic closures, aneurysm exclusion devices, neuropatches, vena cava filters, urinary dilators, endoscopic surgical and wound drainings, bandages, surgical tissue extractors, transition sheaths and dialators, coronary and peripheral guidewires, circulatory support systems, tympanostomy vent tubes, cerebro-spinal fluid shunts, defibrillator leads, percutaneous closure devices, drainage tubes, bronchial tubes, vascular coils, vascular protection devices, vascular intervention devices including vascular filters and distal support devices and emboli filter/entrapment aids, AV access grafts, surgical tampons, and cardiac valves.

All publications and patents mentioned herein are incorporated herein by reference to disclose and describe the specific methods and/or materials in connection with which the publications and patents are cited. The publications and patents discussed herein are provided solely for their disclosure prior to the filing date of the present application. Nothing herein is to be construed as an admission that the present invention is not entitled to antedate such publication or patent by virtue of prior invention. Further, the dates of publication or issuance provided may be different from the actual dates, which may need to be independently confirmed.

The following examples are included to demonstrate preferred embodiments of the invention. It should be appreciated by those of skill in the art that the techniques disclosed in the examples, which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE

Building a 3-D Model of the N-Terminal Regulatory Domain of the Transcription Factor AgrA AgrA is a 28 kDa response regulator protein made up of two domains (Sidote D J, Barbieri C M, Wu T and Stock A M (2008) Structure of the *Staphylococcus aureus* AgrA LytTR Domain Bound to DNA Reveals a Beta Fold with an Unusual Mode of Binding. Structure 16(5):727-735).

The N-terminal domain (residues 1-125) is the receiver domain of a phosphoryl group from the histidine kinase AgrC. Phosphorylation of Asp59 in the putative phosphoryl-histidine binding pocket causes dimerization and activation of the C-terminal DNA-binding domain (residues 143-238), which acts as a transcription factor for promoters P2 and P3 to induce the expression of the genes for AIP and RNAIII, resulting in toxin secretion (e.g., α-hemolysin).

Inactivation of AgrA could be achieved by blocking either the regulatory or the DNA-binding domain. The latter has a large and relatively flat interaction face with DNA, which would be hard to block with a small molecule. Therefore, we opted to target the N-terminal regulatory domain, which presumably has a well defined binding pocket centered on Asp 59. Unfortunately, there is no crystal or NMR solution structure of the N-terminal domain, only a crystal structure of the C-terminal DNA-binding domain of AgrA. However, homology model building is an option. In order to build a model by homology the 3D structure of at least one homologous protein must be known. The degree of sequence identity to the protein of interest must be greater than 20%, the threshold for sequence comparison of two unrelated proteins. A BLAST search of the sequence of AgrA_N against the Protein Data Bank revealed that the regulatory domain of the transcriptional activator NtrC1 (PDB code 1NY5) has a degree of sequence identity of 25% to AgrA_N in the first 100 residues out of a total of 125 residues. The phosphorylated Asp is at residue 59, within this sequence.

Figure 2:
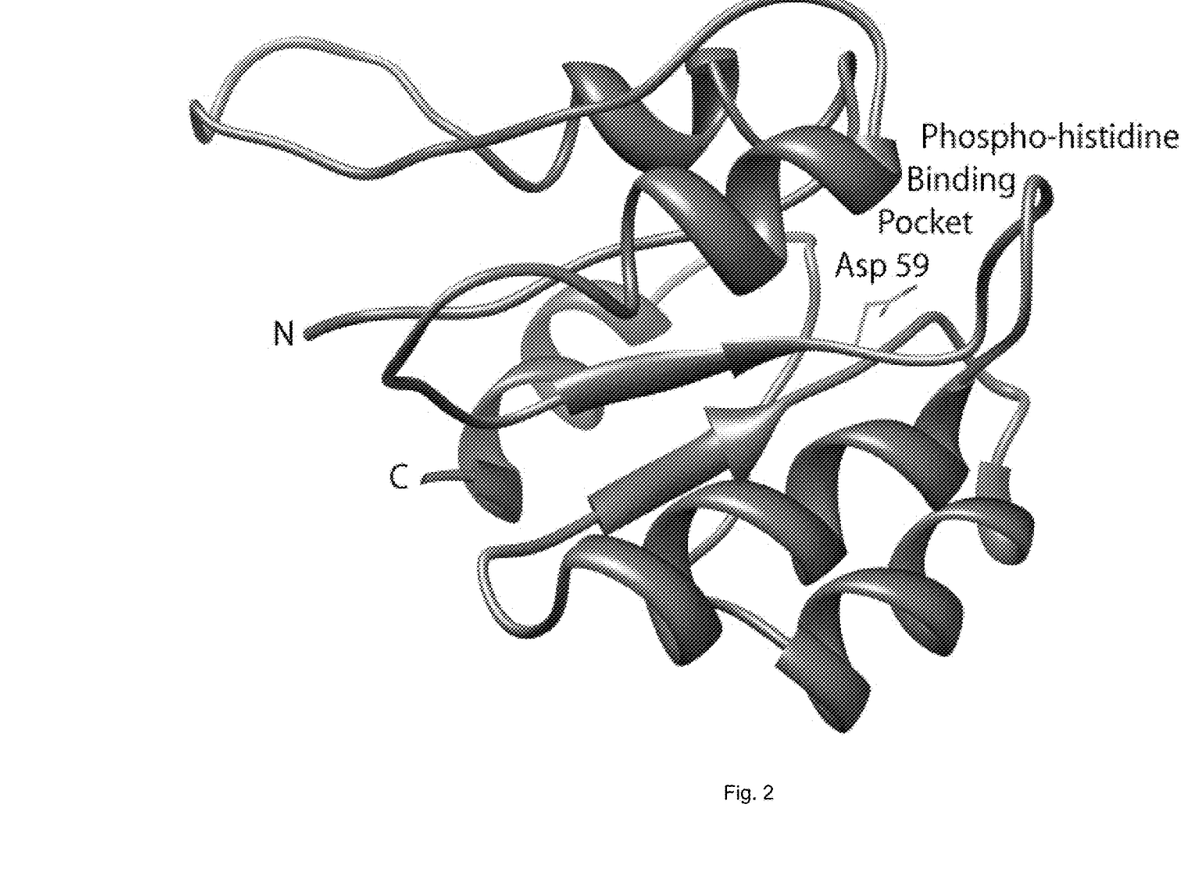
FIG. 2 illustrates a ribbon diagram of the homology-built model of the N-terminal domain of AgrA. Residue Asp 59, shown in stick representation in a pocket on the surface of the protein, is phosphorylated by the histidine kinase AgrC. Phosphorylation of Asp 59 leads to the activation of the C-terminal DNA-binding domain of AgrA, which in turn triggers induction of both AIP and RNAIII, thus leading to toxin (e.g., α-hemolysin) secretion.
Figure 3:
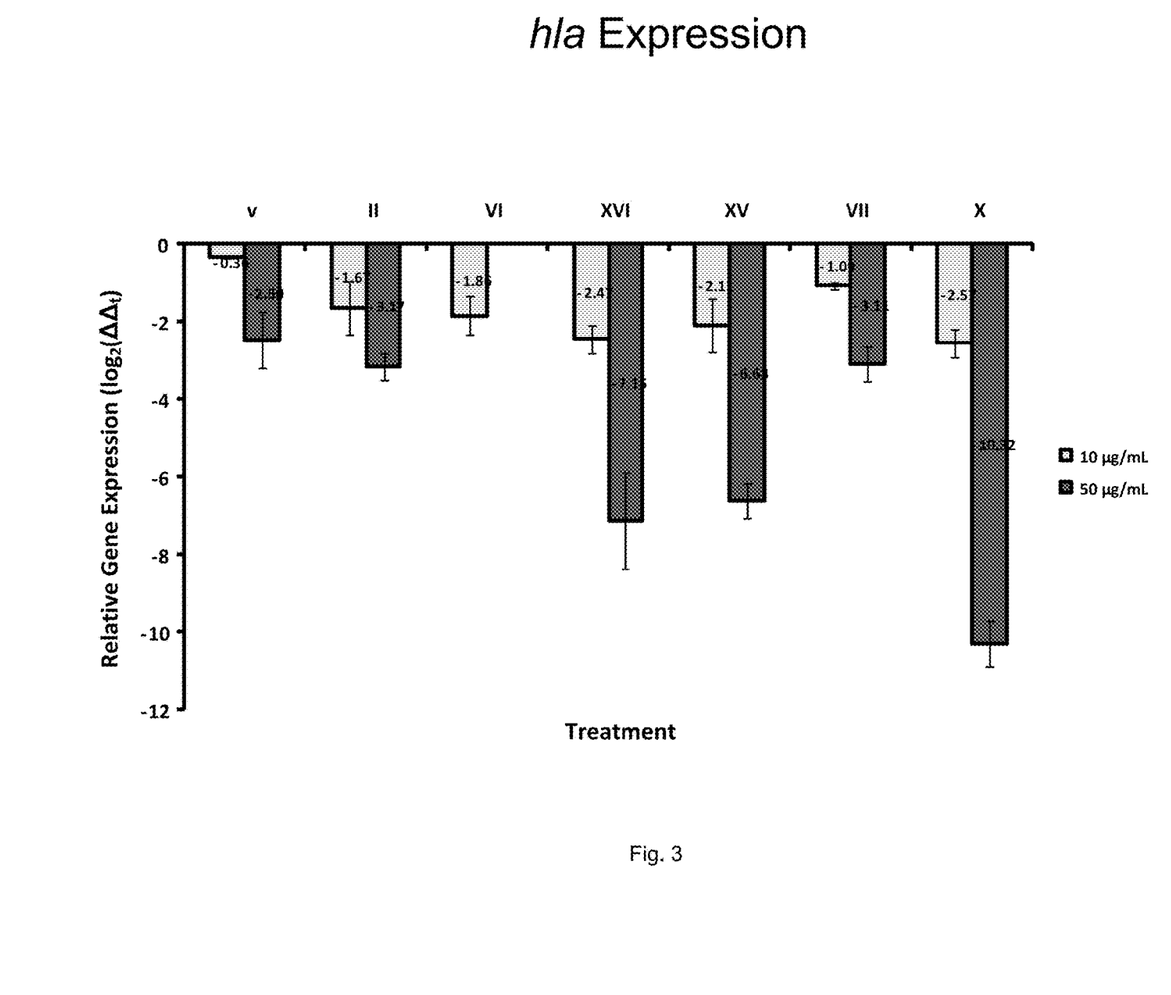
FIG. 3 illustrates a graph showing α-hemolysin gene expression in MRSA strain USA300 treated with compounds II, V, VI, VII, X, XV, and XVI.
Figure 4:
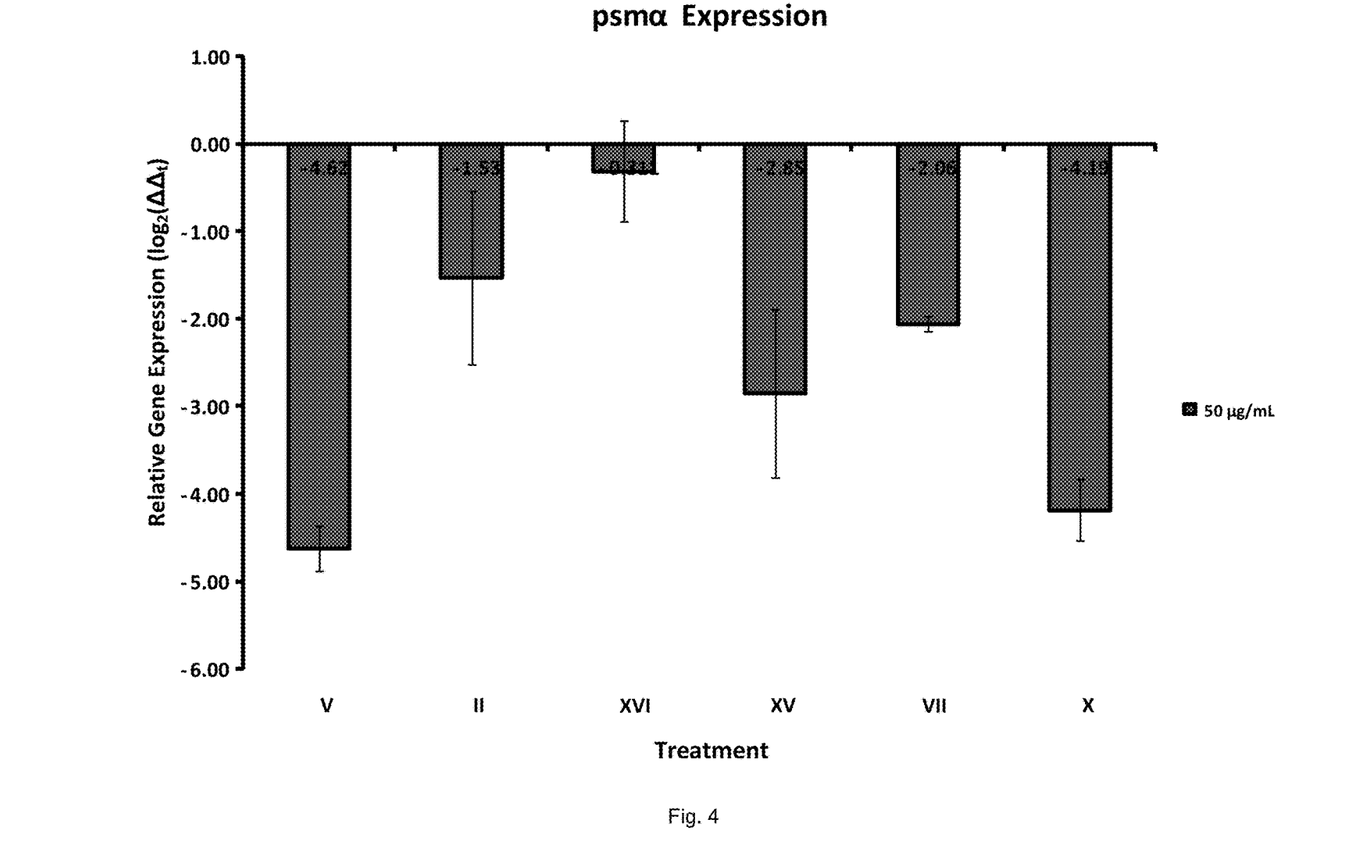
FIG. 4 illustrates a graph showing phenol-soluble modulin-α (psmα) gene expression in MRSA strain USA300 treated with compounds II, V, VI, VII, X, XV, and XVII.
Figure 5:
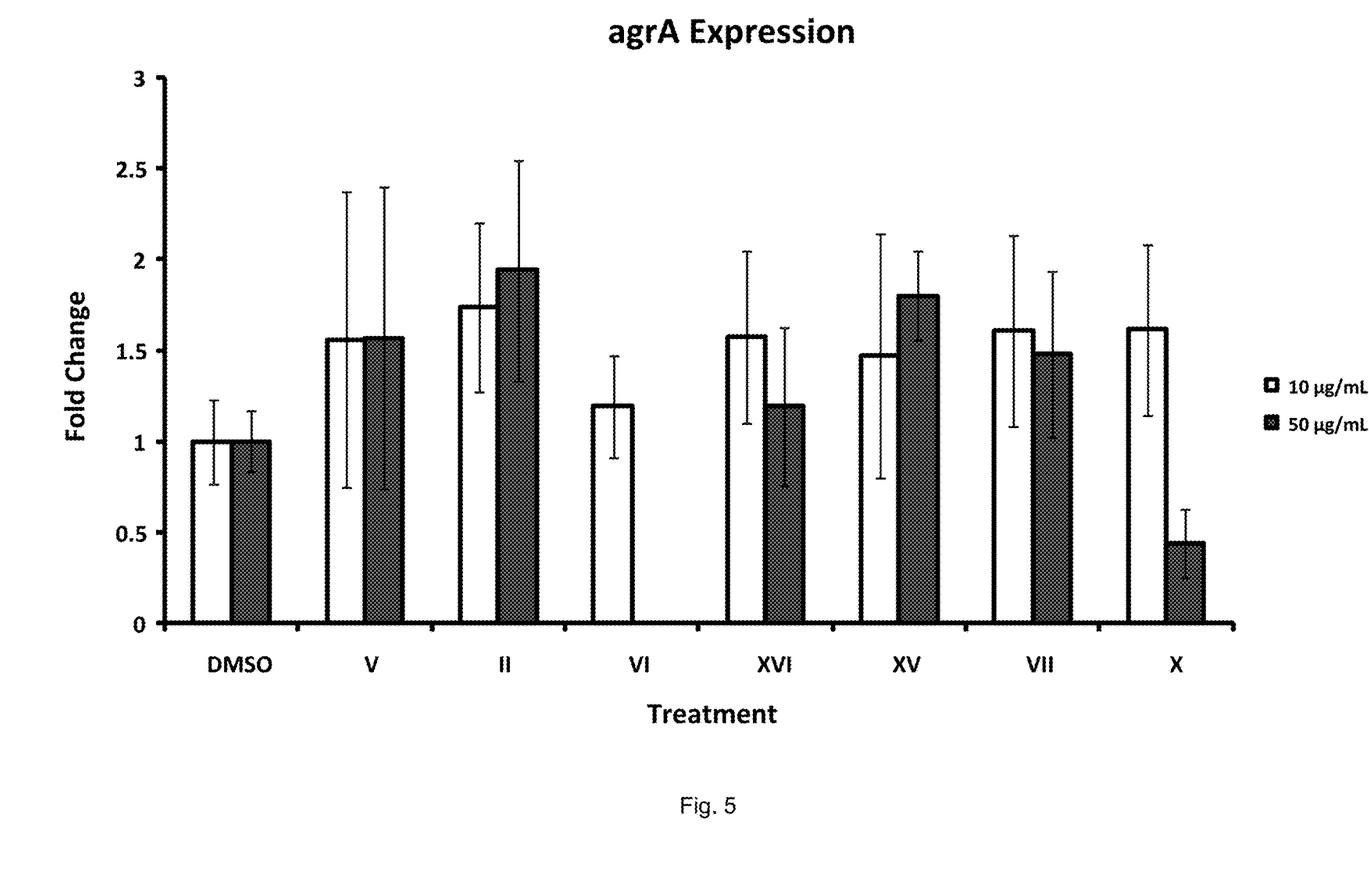
FIG. 5 illustrates a graph showing AgrA gene expression in MRSA strain USA300 treated with compounds II, V, VI, VII, X, XV, and XVI.
Figure 6:
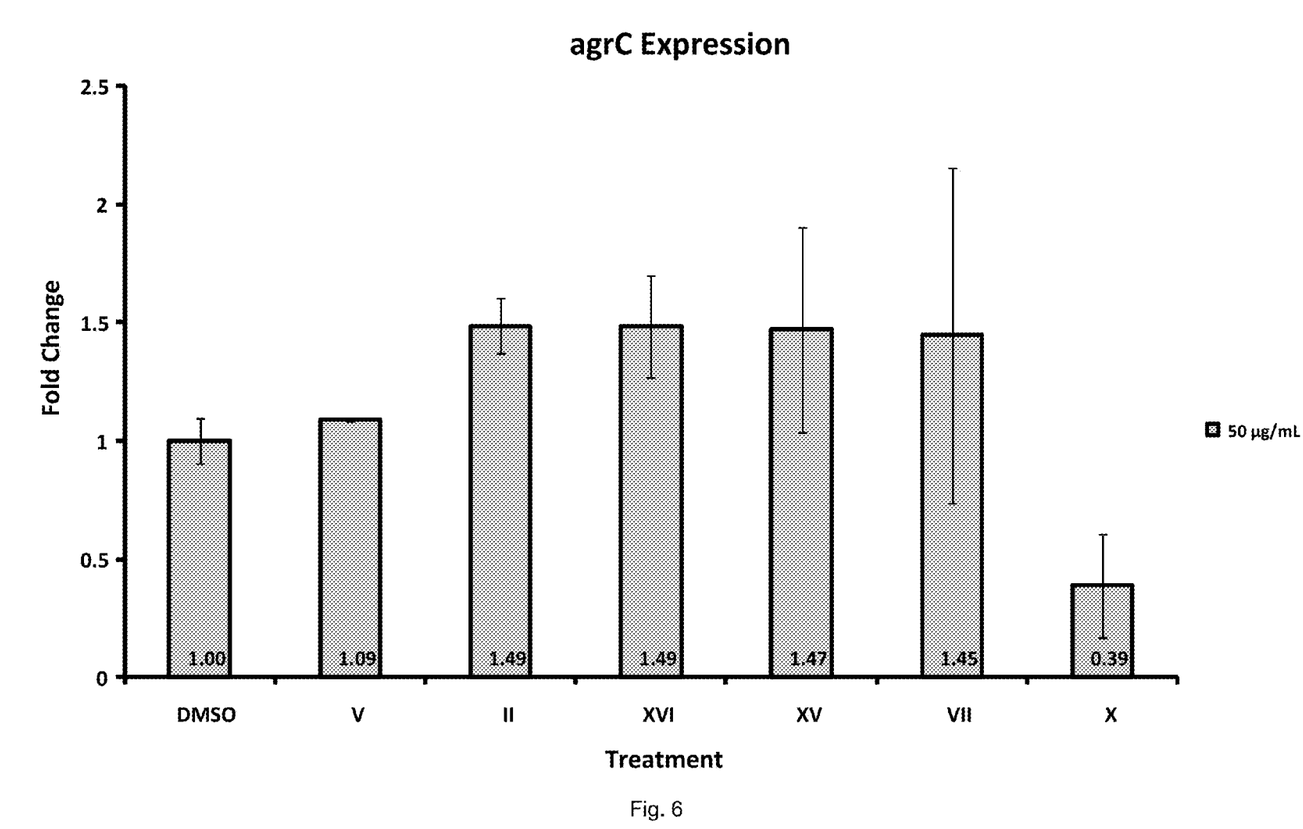
FIG. 6 illustrates a graph showing AgrC gene expression in MRSA strain USA300 treated with compounds II, V, VI, VII, X, XV, and XVI.
Figure 7:
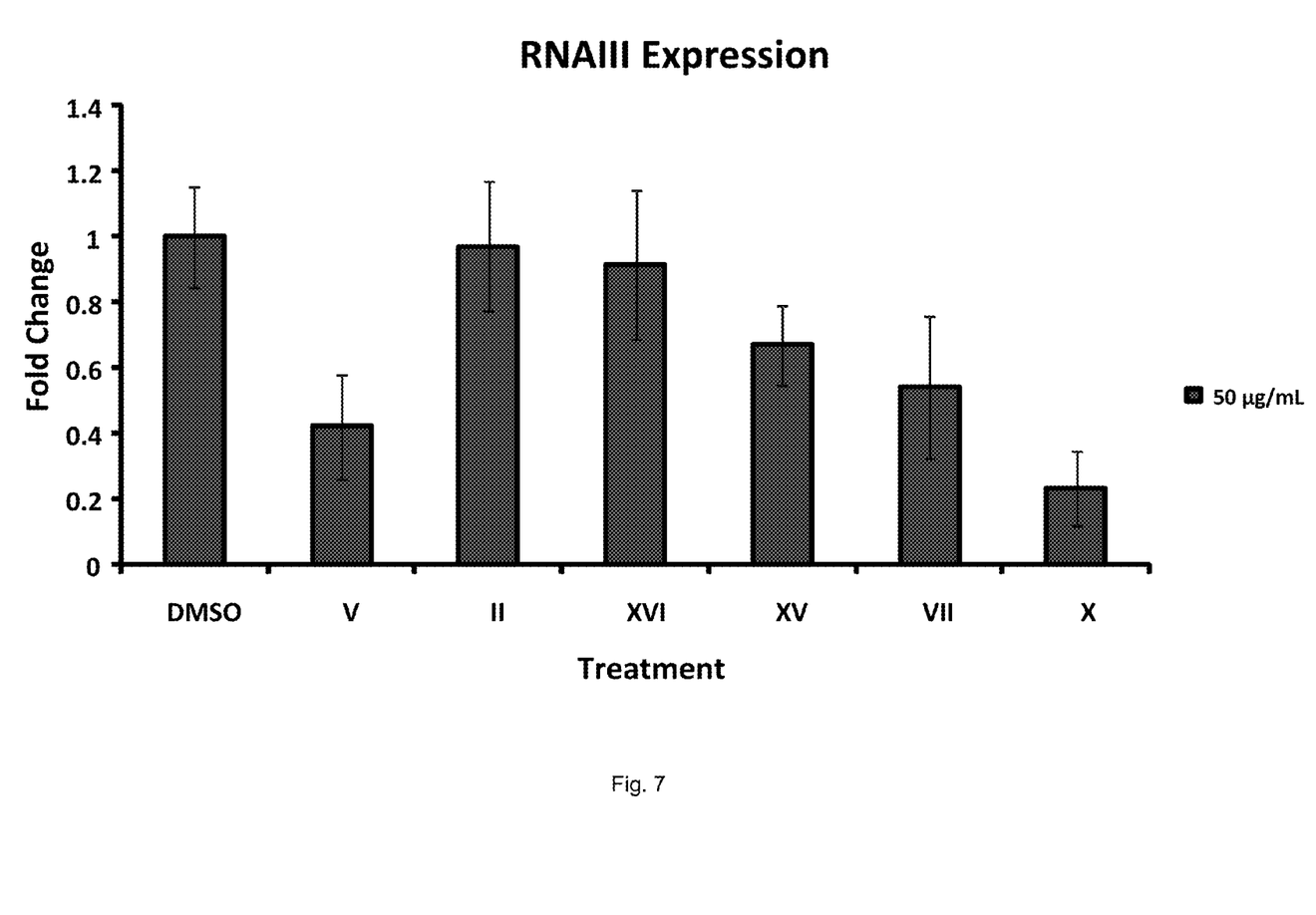
FIG. 7 illustrates a graph showing RNAIII gene expression in MRSA strain USA300 treated with compounds II, V, VI, VII, X, XV, and XVI.

Thus, it was concluded that it would be feasible to build a model of AgrA_N by homology to NtrC1. The program SwissPDBViewer in conjunction with the SwissModel web site were used to generate an initial model of AgrA_N. This model was carefully inspected and subsequently subjected to energy refinement with program CNS. The model is shown in FIG. 2.

Identification of the Phosphoryl-binding Pocket in the 3-D Model of AgrA_N

The model contains a binding pocket encompassing the phosphoryl group receiver Asp 59. The dimensions of the pocket are roughly 10×10×10 Å. Residues lining the binding pocket include Glu 7, Asp8, Asp9, Gln 12 (H-bonded to Asp 59), Leu 62, Val 87 and Lys 110 (salt bridged to Asp 59).

Virtual Screening of the NCI Library of Small-molecule Compounds to Block the Phosphoryl-binding Pocket of AgrA_N Virtual screening was carried out on a multiprocessor Linux-based workstation with program GLIDE within the drug discovery software suite from Schrodinger. The most rigorous scoring function available in GLIDE was employed, as it was proven to be successful in a test case. Screening with this scoring function is considerably slower than with other scoring functions, but it was considered to be well worth the extra time, as concluded from a test case. The screening rate with this scoring function was about 3,000 compounds per day. For an initial screening, the library of 90,000 compounds from the NCI was downloaded from the publicly available ZINC database (Irwin and Shoichet, *J. Chem. Inf. Model.* 2005; 45(1):177-82).

Selecting the Top-scoring Compounds from Virtual Screening for Acquisition

Since the score is a measure of the interaction energy of the compound as docked to the binding pocket of Agr_N the lowest number is the best score, which was −8.63 (arbitrary units). Out of the 90,000 compounds subjected to virtual screening 107 had scores lower than −6.0. These 107 compounds were ordered from the NCI for in vitro testing.

In Vitro Testing of the Efficacy of the Selected Compounds in Inhibition of α-hemolysin Secretion into the Medium During the first phase of in vitro testing the concentration of the compounds was kept constant at 100 mg/L in 2% DMSO. Active compounds were later reexamined at lower concentrations. Some experiments were carried out with the MRSA strain USA300. USA300 is considered a dangerous and widespread Staphylococcal pathogen. Some of these compounds were also assayed for rabbit blood hemolysis inhibition in *Streptococcus pyogenes* and were found to be active.

MRSA strains produce a variety of toxins. It was decided to monitor the levels of α-hemolysin because of the commercial availability of an antibody towards α-hemolysin. Strain USA300 indeed produces α-hemolysin, as demonstrated by an ELISA sandwich assay with a polyclonal antibody to α-hemolysin (Abcam #ab15948) conjugated with horseradish peroxidase (Abcam #ab15949), according to (Crowther J (2000) The ELISA Guidebook, *Methods in Molecular Biology* Vol 149 (Clifton, N.J.) Humana Press). Levels of α-hemolysin were monitored 6 h post induction during the late exponential growth phase.

Seven out of the 107 NCI compounds identified below as compounds I-VII (which correspond to compounds I-VII described above) exhibited significant inhibition of α-hemolysin production without affecting the growth of the bacteria. These seven hits represent 4 separate series, naphthophenol (4 representative compounds), alkyl phenyl sulfonate, alpha hydroxyl troponone, and aminonaphthyridine.

Eight other compounds, listed in Table 1 as Compounds VIII-XVI (which correspond to compounds VIII-XVI described above), were found to exhibit significant inhibition of α-hemolysin production without significantly affecting the growth of the bacteria.

TABLE 1

MRSA USA300 Inhibition Data

| Compound | ELISA α-hemolysin inhibition 1 μg/mL | ELISA α-hemolysin inhibition 10 μg/mL | Rabbit blood hemolysis, 1 μg/mL | Rabbit blood hemolysis, 10 μg/mL |
|---|---|---|---|---|
| I | 28.0 ± 4.4 | 65.0 ± 2.5 | NM | NM |
| II | 21.3 ± 5.2 | 76.0 ± 1.2 | 42.0 ± 2.8 | 69.9 ± 6.1 |
| III | 20.8 ± 3.5 | 28.3 ± 3.4 | NM | NM |
| IV | 40.2 ± 5.2 | 73.6 ± 2.2 | NM | NM |
| V | 23.0 ± 1.3 | 88.4 ± 1.5 | 9.0 ± 1.3 | 63.6 ± 6.6 |
| VI | 55.2 ± 5.8 | 76.3 ± 11.2 | 40.0 ± 3.5 | 80.2 ± 7.0 |
| VII | 31.3 ± 9.0 | 61.0 ± 14.8 | 38.6 ± 6.4 | 55.6 ± 9.3 |
| VIII | NM | 56.3 ± 1.7 | NM | NM |
| IX | 15.9 ± 4.2 | 41.9 ± 8.2 | 6.0 ± 7.5 | 21.3 ± 6.1 |
| X | 33.0 ± 3.6 | 62.3 ± 1.8 | 71.1 ± 5.9 | 83.7 ± 8.5 |
| XI | NM | 36.3 ± 8.2 | NM | NM |
| XII | NM | 29.1 ± 11.0 | NM | NM |
| XIII | NM | 35.6 ± 12.5 | NM | NM |
| XIV | NM | 26.7 | NM | NM |
| XV | 49.4 ± 4.6 | 53.0 ± 5.9 | 34.3 ± 6.9 | 84.7 ± 6.7 |
| XVI | 0.0 ± 7.0 | 68.8 ± 11.3 | 49.0 ± 2.2 | 76.6 ± 8.1 |

NM, not measured

Some of these compounds (i.e., compounds II, V, VI, VII, IX, X, XV, and XVI) were also assayed for rabbit blood hemolysis inhibition in *Streptococcus pyogenes* and were found to be active as shown in Table 2. Moreover, compounds II, V, VI, VII, X, XV, and XVI were found to inhibit, α-hemolysin, phenol-soluble modulin-α (psmα), AgrA, AgrC and RNAIII gene expression in MRSA strain USA300 (FIGS. 3-7).

TABLE 2

Inhibition of rabbit blood hemolysis by *Streptococcus pyogenes*

| Compound | 1 μg/mL | 10 μg/mL |
|---|---|---|
| II | 4.7 ± 5.9 | 15.9 ± 7.4 |
| V | 25.2 ± 7.1 | 73.6 ± 7.4 |
| VI | 73.0 ± 4.2 | 94.8 ± 5.4 |
| VII | 23.1 ± 4.5 | 19.4 ± 7.3 |
| IX | NM | 14.4 ± 3.6 |
| X | 23.2 ± 3.3 | 68.7 ± 9.5 |
| XV | 25.4 ± 4.1 | 43.6 ± 4.3 |
| XVI | 5.1 ± 2.8 | 33.4 ± 4.4 |

Figure 8:
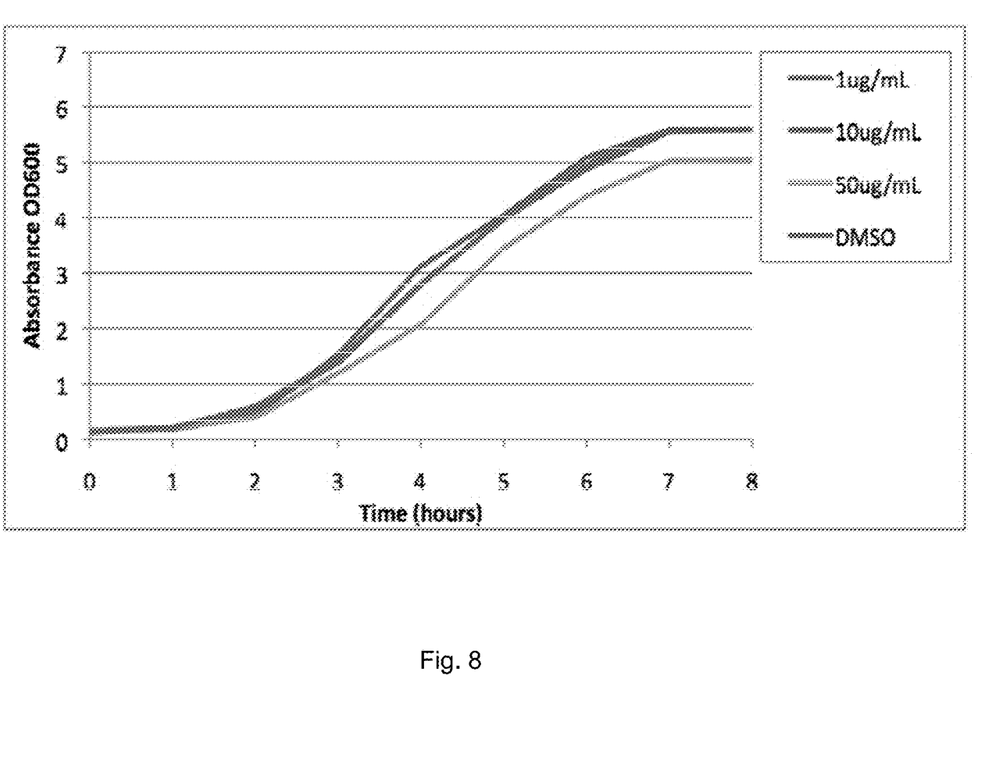
FIG. 8 illustrates a representative growth curve of *S. aureus* USA300 incubated with varying concentrations of compound X (i.e., diflunisal).

Among the most efficacious compounds were the four biaryl compounds V, VI and X. Bacterial growth was not affected by the presence of the compounds in the culture medium (FIG. 8).

Measurement of α-toxin and RNAIII Gene Expression by qRT-PCR

The effect of the compounds VII, X, XII, and XV on the transcription of hla and RNAIII was measured by qRT-PCR. *S. aureus* USA300 was incubated at 37° C. for 6 h in the presence of 0, 10, or 50 μg/ml of the compounds. The cultures were harvested, and total RNA was isolated using the RiboPure—bacterial RNA isolation kit (Ambion) with additional DNase I treatment. RNA yield and purity were assessed by measuring the ratio of UV absorbance at 260 and 280 nm, and the integrity of the RNA was assessed on a 1% denaturing agarose gel. High integrity RNA had two clear bands without smearing, indicating no fragmentation of 23S and 16S rRNA.

The hup gene, encoding a histone-like protein that binds DNA, was used as the control housekeeping gene in the qRT-PCR experiments, and none of the inhibitors changed the expression of the hup gene. Real-time RT-PCR reactions were conducted using a SYBR—green mix (Bio-Rad). The data were analyzed using the $\Delta\Delta C_t$ and are represented as $\log_2$ of the treated sample/control sample (DMSO only).

Figure 9:
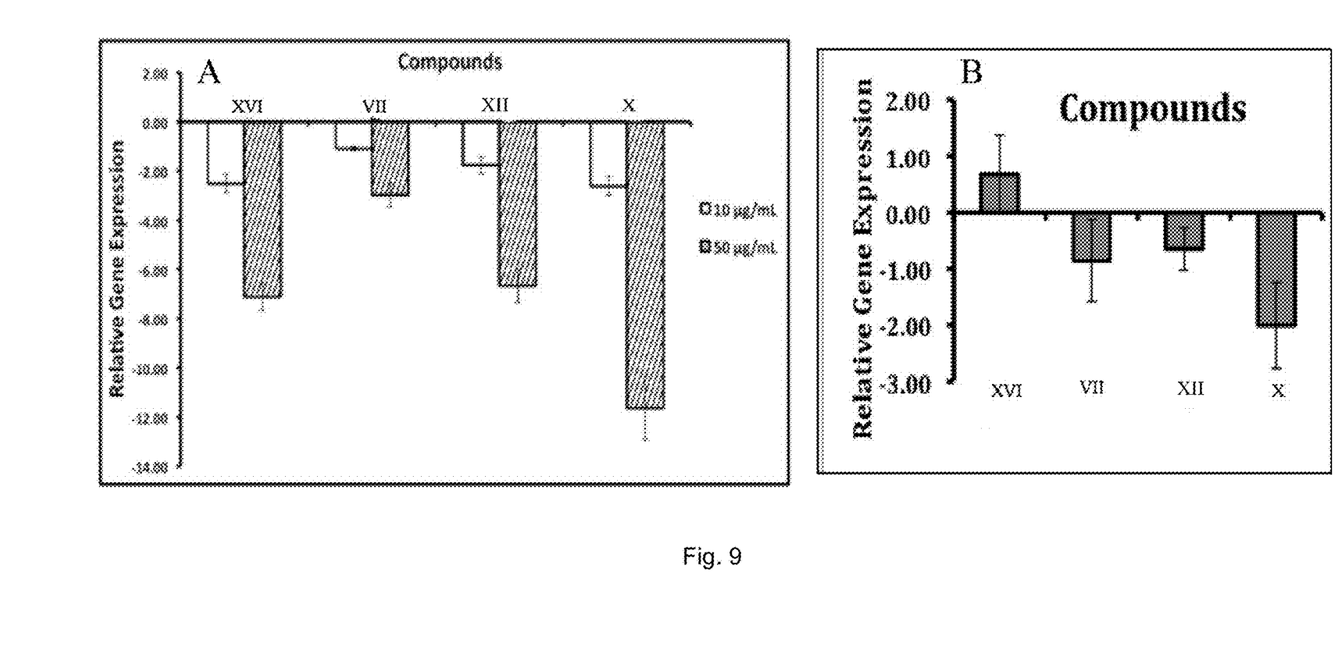
FIG. 9 illustrates graphs showing inhibition of (A) hla and (B) RNAIII transcription by compounds VII, X, XII, and XV. Gene expression of hla is reduced by inhibitors at 10 and 50 μg/ml, whereas RNAIII was reduced only in 50 μg/mL diflunisal. Relative gene expression is defined as $\log_2$ (treatment/DMSO) in duplicate (B) or triplicate (A) measurements.

As shown in FIG. 9, all four compounds inhibited transcription of hla in a dose-dependent manner. Diflunisal (compound X) at 50 μg/mL reduced hla expression ~3000-fold. These findings are consistent with diminished levels of Hla measured in cultures incubated with the four pilot compounds. Only treatment of *S. aureus* with diflunisal resulted in a significant reduction in RNAIII expression, suggesting that diflunisal-like compounds likely target multiple regulatory pathways, including agr, sar, A and sigB.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

Having described the invention, the following is claimed:

1. A pharmaceutical composition comprising an accessory gene regulator A (AgrA) antagonist having the formula:

(VI)

and pharmaceutically acceptable salts thereof, and an antibiotic.

2. A pharmaceutical composition comprising an accessory gene regulator A (AgrA) antagonist having the formula:

wherein $R_1$ and $R_2$ are each independently selected from the group consisting of H, hydroxy, carboxy, lower alkoxy, lower alkoxyhydroxy, lower alkyl, alkenyl, sulfonic, and halo; $R_3$ is a C2-C6 lower alkyl;

and pharmaceutically acceptable salts thereof, and an antibiotic.

* * * * *